United States Patent
Roeder et al.

(10) Patent No.: US 10,130,501 B2
(45) Date of Patent: Nov. 20, 2018

(54) DELIVERY DEVICE WITH AN EXTENSION SHEATH AND METHODS OF USING THE SAME

(71) Applicant: Cook Medical Technologies LLC, Bloomington, IN (US)

(72) Inventors: Blayne A. Roeder, Bloomington, IN (US); Joel Ondersma, Bloomington, IN (US); Edwin E. Macatangay, Bloomington, IN (US); Siddharth Vad, Irvine, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 418 days.

(21) Appl. No.: 14/637,824

(22) Filed: Mar. 4, 2015

(65) Prior Publication Data

US 2015/0173925 A1    Jun. 25, 2015

Related U.S. Application Data

(63) Continuation-in-part of application No. 13/795,923, filed on Mar. 12, 2013, now Pat. No. 9,439,793.

(51) Int. Cl.
| | | |
|---|---|---|
| *A61F 2/954* | (2013.01) | |
| *A61F 2/966* | (2013.01) | |
| *A61F 2/07* | (2013.01) | |
| *A61F 2/06* | (2013.01) | |

(52) U.S. Cl.
CPC .............. *A61F 2/966* (2013.01); *A61F 2/954* (2013.01); *A61F 2/07* (2013.01); *A61F 2002/061* (2013.01); *A61F 2002/067* (2013.01); *A61F 2220/0033* (2013.01)

(58) Field of Classification Search
CPC .......... A61F 2002/067; A61F 2002/061; A61F 2/966; A61F 2/954; A61F 2/07
See application file for complete search history.

(56) References Cited

U.S. PATENT DOCUMENTS

| | | |
|---|---|---|
| 5,383,852 A | 1/1995 | Stevens-Wright |
| 5,429,617 A | 7/1995 | Hammersmark et al. |
| 5,746,766 A | 5/1998 | Edoga |
| 5,921,978 A | 7/1999 | Thompson et al. |
| 6,285,903 B1 | 9/2001 | Rosenthal et al. |
| 6,520,934 B1 | 2/2003 | Lee et al. |
| 6,695,875 B2 | 2/2004 | Stelter et al. |

(Continued)

FOREIGN PATENT DOCUMENTS

| | | |
|---|---|---|
| WO | WO 99/47078 A1 | 9/1999 |
| WO | WO 01/67993 A2 | 9/2001 |

(Continued)

OTHER PUBLICATIONS

Extended International Search Report for European Patent Application No. EP 14275023, dated Jun. 2, 2014, 6 pages.

(Continued)

*Primary Examiner* — Anh T Dang
(74) *Attorney, Agent, or Firm* — Brinks Gilson & Lione

(57) ABSTRACT

Methods for delivering and deploying an endovascular graft to the common and internal iliac arteries are described. A system including a pre-loaded delivery device with a releasably attached extension cannula and an extension sheath for use with such methods is also described.

12 Claims, 14 Drawing Sheets

(56) References Cited

U.S. PATENT DOCUMENTS

| | | |
|---|---|---|
| 6,827,726 B2 | 12/2004 | Parodi |
| 6,849,087 B1 | 2/2005 | Chuter |
| 7,108,715 B2 | 9/2006 | Lawrence-Brown et al. |
| RE39,668 E | 5/2007 | Bagaoisan et al. |
| 7,344,556 B2 | 3/2008 | Seguin et al. |
| 7,393,357 B2 | 7/2008 | Stelter et al. |
| 7,651,521 B2 | 1/2010 | Ton et al. |
| 7,815,608 B2 | 10/2010 | Schafersman et al. |
| 7,815,671 B2 | 10/2010 | Wright et al. |
| 7,867,270 B2 | 1/2011 | Hartley et al. |
| 7,930,014 B2 | 4/2011 | Huennekens et al. |
| 7,998,186 B2 | 8/2011 | Hartley |
| 8,012,193 B2 | 9/2011 | Hartley et al. |
| 8,014,849 B2 | 9/2011 | Peckham |
| 8,043,354 B2 | 10/2011 | Greenberg et al. |
| 8,092,509 B2 | 1/2012 | Dorn et al. |
| 8,118,854 B2 | 2/2012 | Bowe |
| 8,262,718 B2 | 9/2012 | Chuter et al. |
| 8,641,752 B1 * | 2/2014 | Holm .................. A61F 2/966 623/1.12 |
| 8,690,815 B2 | 4/2014 | Porter et al. |
| 2005/0159773 A1 | 7/2005 | Broome et al. |
| 2005/0255317 A1 | 11/2005 | Bavaro et al. |
| 2007/0083215 A1 | 4/2007 | Hamer et al. |
| 2007/0123910 A1 | 5/2007 | Hartley et al. |
| 2007/0250154 A1 | 10/2007 | Greenberg et al. |
| 2008/0221656 A1 | 9/2008 | Hartley et al. |
| 2008/0234796 A1 * | 9/2008 | Dorn .................. A61F 2/966 623/1.11 |
| 2010/0016943 A1 | 1/2010 | Chobotov |
| 2011/0270375 A1 | 11/2011 | Hartley et al. |
| 2011/0270376 A1 | 11/2011 | Hartley |
| 2011/0295111 A1 | 12/2011 | Hansis et al. |
| 2012/0172968 A1 | 7/2012 | Chuter et al. |
| 2012/0226341 A1 | 9/2012 | Schreck et al. |
| 2013/0030514 A1 | 1/2013 | Kasprzak et al. |
| 2013/0204342 A1 | 8/2013 | Kasprzak et al. |

FOREIGN PATENT DOCUMENTS

| | | |
|---|---|---|
| WO | WO 2004/047885 A2 | 6/2004 |
| WO | WO 2004/089249 A1 | 10/2004 |
| WO | WO 2005/037141 A2 | 4/2005 |
| WO | WO 2007/124053 A1 | 11/2007 |
| WO | WO 2010/127040 A1 | 11/2010 |
| WO | WO 2011/116308 | 9/2011 |

OTHER PUBLICATIONS

International Search Report and Written Opinion for PCT/US2011/029037, dated Jul. 21, 2011, 10 pages.
International Preliminary Report on Patentability for PCT/US2011/029037, dated Mar. 22, 2012, 6 pages.
Response to International Search Report and Written Opinion, dated Jan. 19, 2012, 11 pages.
International Patent Examination Report No. 1 for Australian Patent Application No. 2012200735 dated Jun. 20, 2012, 8 pages.
Office Action/Restriction received in related U.S. Appl. No. 13/635,573 dated May 2, 2013, 7 pages.
Response to Office Action/Restriction filed in related U.S. Appl. No. 13/635,573 dated May 9, 2013, 12 pages.
Office Action received in related U.S. Appl. No. 13/635,573 dated Aug. 6, 2013, 13 pages.
Response to Office Action filed in related U.S. Appl. No. 13/635,573 dated Aug. 15, 2013, 14 pages.
Notice of Allowance received in related U.S. Appl. No. 13/635,573 dated Oct. 29, 2013, 11 pages.
Extended European Search Report for corresponding EP 16275039 dated Jun. 17, 2016, 8 pages.

* cited by examiner

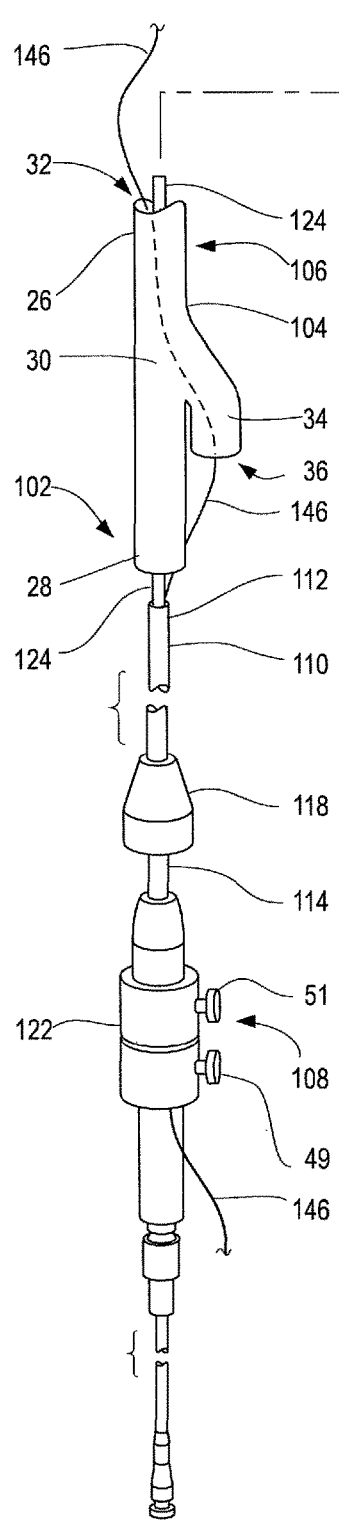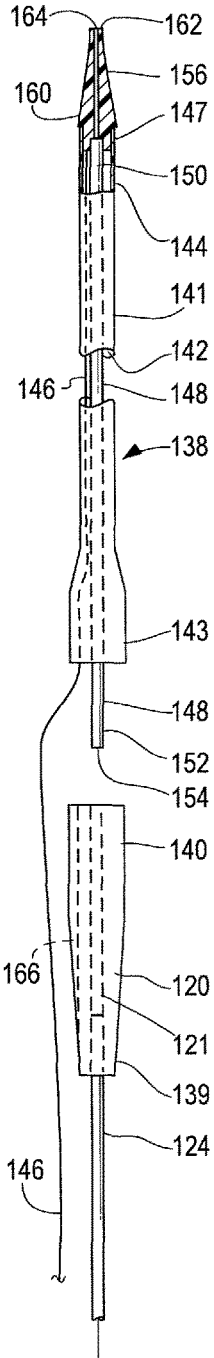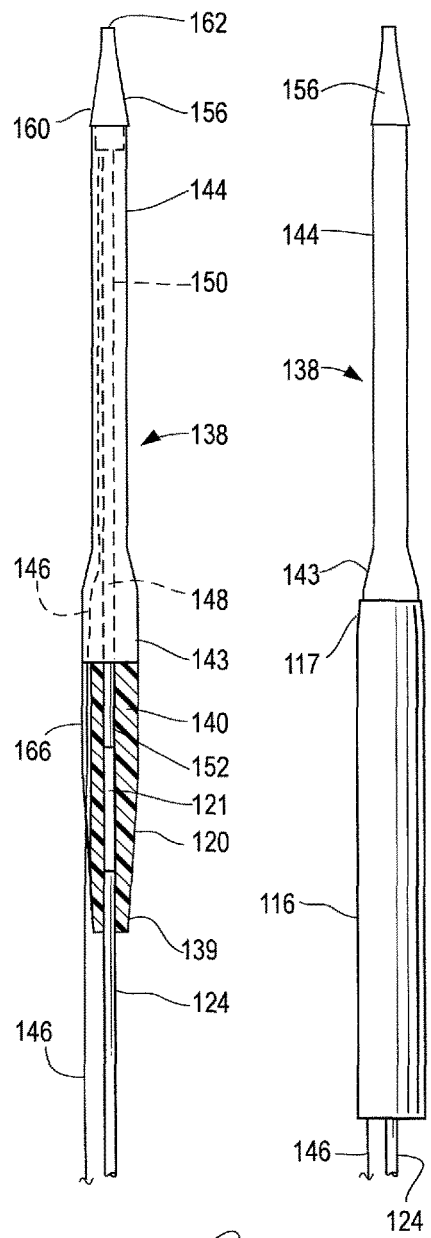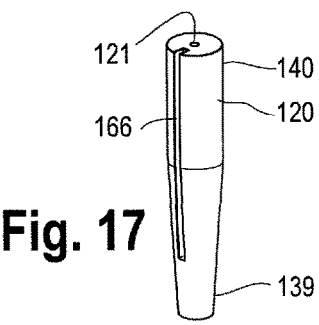
Fig. 14  Fig. 15  Fig. 16
Fig. 17

DELIVERY DEVICE WITH AN EXTENSION SHEATH AND METHODS OF USING THE SAME

This application is a continuation-in-part application of U.S. Ser. No. 13/795,923 filed Mar. 12, 2013.

BACKGROUND

This invention relates generally to medical devices and methods of using the same, and more particularly, to an endovascular stent graft delivery device and methods for placement and deployment of the graft in the lumen of a branched vessel such as an iliac artery.

Stent grafts may be inserted into an anatomical vessel or duct for various purposes. For example, stent grafts are used for treatment of vasculature in the human or animal body to bypass a repair or defect in the vasculature or to maintain or restore patency in a formerly blocked or constricted passageway. For example, a stent graft may extend proximally and/or distally away from a vascular defect, including a diseased portion of an aneurysm, and engage a healthy portion of a vessel wall. In many cases, however, such a damaged or defective portion of the vasculature may include a branched or side vessel such as a common iliac artery and/or an internal iliac artery extending from the common iliac artery. Commonly, to repair a defect in these branched vessels, a stent graft is provided which, when deployed in the common iliac artery, has a side branch or arm positioned towards the opening to the internal iliac artery and then, if desired, another stent graft can be deployed through the side branch into the internal iliac artery to bypass a diseased portion thereof and restore the blood flow path to the internal iliac artery.

Generally, when deploying an endovascular stent graft into a vessel lumen, it is possible to obtain access to such a lumen from one or both ends of the vessel where necessary, thereby facilitating placement of a graft in the desired portion of the lumen. However, the internal iliac artery, which extends from the common iliac artery below the aortic bifurcation, is a blind vessel because there is no practical way of performing a minimally invasive endovascular procedure into that vessel other than by entry from the common iliac artery.

Access to and introduction of a stent graft into the common and/or internal iliac arteries and successful deployment of a stent graft in such vessels may often depend upon a favorable layout of the arteries and, in many cases, access is difficult. One known approach that has been used includes accessing the target location(s) within the vessels by a contralateral or crossover approach. In other words, a delivery device having a guide wire carried thereon may be first introduced into a common iliac artery and the wire snared and pulled though the delivery device (while the device is still sheathed) from the contralateral side so that it extends across the aortic bifurcation. The wire is often covered by a catheter to allow manipulation of the wire during snaring. In this way, a pathway is created in the vasculature to facilitate the introduction and deployment of a stent graft to the target location in the contralateral internal iliac artery.

As endovascular techniques become more refined, physicians continue to seek novel alternative and simplified approaches to treating diseased vessels, including delivery devices that facilitate introduction and deployment of stent grafts into branched and/or blind vessels that are difficult to access and traverse. For example, accessing the target location(s) within the common and/or internal iliac artery using a low-profile delivery device for placing a stent graft in one or more branched vessels that eliminates the need to snare and pull a pre-loaded guide wire though the sheathed delivery device and over the aortic bifurcation is desirable. A method for introducing a stent graft into the common and/or internal iliac arteries and a delivery device to enable such a method to be practiced is described herein.

While this invention will be generally discussed in relation to a delivery device for a stent graft and method of deployment thereof into a common iliac artery where it is necessary to extend a side branch from a main portion or body of the graft into an internal iliac artery, it is also contemplated that the invention is not so limited and may relate to any body or vessel lumen in which such a deployment is necessary or desired.

SUMMARY

The present disclosure provides a prosthesis delivery device and methods for delivering and deploying a prosthesis into one or more vessels. In one example, the device comprises an inner cannula having a proximal end and a nose cone dilator extending proximally from the proximal end of the inner cannula. The nose cone has a proximal end and a distal end and a groove extending longitudinally along at least a portion of an outer surface of the nose cone between the proximal and distal ends. An extension cannula having a proximal end and a distal end is releasably attached to the proximal end of the nose cone and an extension sheath is coaxial with at least a portion of the extension cannula. The extension sheath has a proximal end and a distal end and a lumen extending between the proximal and distal ends. The device further comprises a main sheath having a proximal end, a distal end and a lumen extending there between, wherein the main sheath has a first position in which a proximal end of the main sheath is coaxial with the distal end of the extension sheath and a second position in which the proximal end of the main sheath is distal to the distal end of the extension sheath. A pre-loaded guide wire extends proximally at least partially through the lumen of the main sheath, through the groove formed in the nose cone and proximally at least partially through the lumen of the extension sheath.

A method for treating a diseased vessel is also described. In one example, the method comprises introducing a delivery device into a patient's vasculature. The delivery device comprises an inner cannula having a proximal end and a stent graft releasably coupled to the proximal end of the inner cannula, a nose cone dilator extending proximally from the proximal end of the inner cannula, an extension cannula having a proximal end and a distal end releasably connected to the proximal end of the nose cone, an extension sheath coaxial with at least a portion of the extension cannula and a main sheath having a proximal end, a distal end and a lumen extending there between. The main sheath has a first position in which a proximal end of the main sheath is coaxial with the distal end of the extension sheath and a second position in which the proximal end of the main sheath is distal to the distal end of the extension sheath. The method further comprises retracting the main sheath to move it from the first position to the second position to expose at least a portion of the stent graft, releasing the extension cannula and extension sheath from the proximal end of the nose cone and removing the extension cannula and extension sheath from the patient's vasculature.

BRIEF DESCRIPTION OF THE DRAWINGS

FIG. 14 illustrates one example of a pre-loaded delivery device with an extension cannula and an extension sheath.

FIG. 15 illustrates the delivery device of FIG. 14 with the extension cannula mated with the nose cone of the delivery device.

FIG. 16 illustrates the delivery device of FIG. 15 with a sheath extending proximally to and coaxially over the nose cone.

FIG. 17 illustrates one example of a nose cone having a groove formed along at least a portion of the outer surface thereof.

DETAILED DESCRIPTION

Throughout this specification the terms "proximal" and "proximally" are used for a position or direction towards the patient's heart and the terms "distal" and "distally" are used for a position or direction away the patient's heart. The term "ipsilateral" is used to indicate that the diseased vessel(s) being accessed during a given procedure are on the same side of the body (right or left) as the vascular access device/introducer, while "contralateral" signifies that the vessel(s) of interest are on the opposite side of the body.

The embodiments described below are in connection with systems and methods for the introduction and deployment of an implantable medical device in a vessel, such as endovascular prosthesis, but could also be used for deploying a range of implantable medical devices including, but not limited to, stents, stent grafts, occlusion devices and the like.

Figure 1:
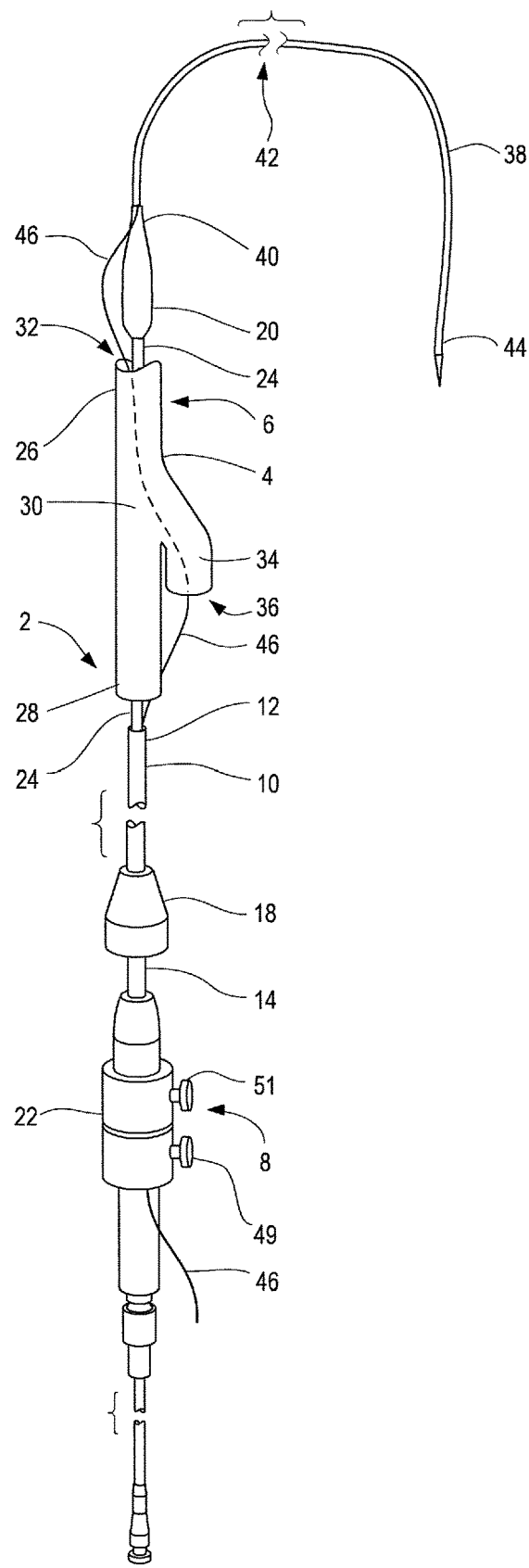
FIG. 1 shows one example of a pre-loaded delivery device for introducing, placing and deploying a stent graft into a patient's vasculature.

Referring to FIG. 1, an example of a stent graft delivery device is shown generally at 2 with a stent graft 4 mounted onto it. During the medical procedure to position and deploy the stent graft 4, the proximal end 6 of the device 2 will travel through the vessel lumen to a desired deployment site. The distal external manipulation section 8 which may include a handle portion, which is acted upon by a user to manipulate the device, remains outside of the patient throughout the procedure. The delivery device 2 is preferably "pre-loaded", or in other words, before the delivery device is introduced into the patient's vasculature, it is pre-assembled with mechanisms that facilitate graft delivery and deployment already arranged thereon. The delivery and deployment mechanisms may include, for example, one or more guide wires, catheters, sheaths, stent grafts and combinations thereof, which are arranged on and/or are carried by the device 2 and which remain in place during delivery of the stent graft 4 into a patient's vasculature. In one non-limiting example, the delivery device 2 may include one or more mechanisms that aid in the placement and deployment of a stent graft 4 in the common iliac artery and/or one or more mechanisms that aid in the placement and deployment of an additional or side branch extension stent graft in an internal iliac artery in accordance with the systems and methods described herein.

More specifically, as shown in FIG. 1, the device 2 includes a pusher catheter 10 having a proximal end portion 12 and a distal end portion 14. In one example, the pusher catheter 10 has at least one lumen extending between the proximal 12 and distal 14 end portions. A sleeve or sheath 16, which may be operated by a sheath manipulator 18, is preferably mounted co-axially over the pusher catheter 10. In the ready-to-deploy position, the sheath 16 extends proximally to the nose cone dilator 20 and covers a stent graft 4 carried on the device 2. As illustrated in FIG. 1, however, the sheath 16 is withdrawn so that the stent graft 4 is exposed to show detail of the assembly. A handle 22 at the distal end 14 of the pusher catheter 10 enables manipulation of various components of the device 2.

As shown in FIG. 1, a cannula 24 extends through the lumen of the pusher catheter 10, from the distal end 8 of the device to immediately distal of the nose cone dilator 20. A branched stent graft 4 may be retained on the device 2, and, in one example, the proximal end of the graft 26 may be secured to the cannula 24 by a retention arrangement immediately distal of the nose cone dilator 20. The branched stent graft 4 may also be retained at its distal end 28 by another retention arrangement on the device 2. Retention may be by various means, and in one non-limiting example, may include one or more loops or stitches of suture material which are engaged with a trigger wire extending from an aperture (not shown) in the cannula 24. In another example, a trigger wire (not shown) may pierce or be woven through the stent graft 4 directly, thus, retaining the graft against the cannula 24 until the trigger wire(s) is removed. However, it is also contemplated that other types and methods of proximal and/or distal restraint may be used including various diameter reducing ties, fasteners or the like that are suitable for removably securing the stent graft 4 on the device 2. The retaining mechanisms may be placed in any suitable arrangement or location so that the graft 4 is removably secured to the device 2. The proximal and/or distal ends of the stent graft 4 may be released from this retention arrangement by releasing the one or more mechanisms (i.e. releasing a suture and trigger wire or any other type of mechanisms that may be used in combination with or in place of such sutures) during deployment of the graft, thereby facilitating at least partial deployment of the stent graft 4 within a vessel lumen.

The stent graft 4 carried on the device 2 preferably has a substantially tubular main body 30 having a proximal end portion 26 and a distal end portion 28 with a main lumen 32 extending through the main tubular body 30. A side branch 34, also preferably having a substantially tubular body defining a lumen 36, preferably extends from the main body 30 and may be integrally formed with the main body, or alternatively, the side branch 34 may be a separately formed component that is secured to the main body 30 such as by stitching, bonding, adhesive or the like. The lumen 32 of the main body and the lumen 36 of the side branch are preferably in fluid communication. In one example, both the main body 30 and the side branch 34 are constructed from of one or more biocompatible materials including, but not limited to, polyesters, fluorinated polymers and polyurethanes and/or may be made from natural or organic materials. The materials may also be subjected to surface modifications or coatings.

In a preferred example, the stent graft 4 is configured to be deployed into the vasculature of a patient with the main tubular body 30 being located in the common iliac artery and the side branch being directed towards an internal iliac artery of the common iliac artery, although other stent graft configurations for deployment into various other body vessels are also contemplated depending on various factors including, but not limited to the particular vessel(s) being treated and/or the location of a particular damaged or diseased portion of a vessel.

As shown in FIG. 1, an extension sheath 38 extends from the proximal tip 40 of the nose cone dilator 20. The extension sheath 38 is preferably flexible to allow it to be advanced through a patient's vasculature, and at least a portion of the extension sheath is, in one example, curved in a hook or U-shaped configuration. However, the extension sheath 38 may have a variety of shapes and configurations depending on the procedure being performed and the vasculature though which the delivery device is being navigated. A lumen 42 extends through the extension sheath 38, and the sheath may terminate in a proximal tip 44. Extension sheath 38 is described in further detail below in connection with FIGS. 14-16.

The delivery device 2 is preferably pre-loaded with a guide wire 46. This pre-loaded guide wire 46 runs along the length of the delivery device and extends proximally from the proximal end 12 of the pusher catheter 10 and runs outside of the distal end portion 28 of the main graft body, and into the lumen 36 of the side branch 34. The guide wire 46 continues to run proximally through the lumen 36 of the side branch 34, out of the proximal end 26 of the main graft lumen 32 and, in a first "pre-deployment" position, the guide wire 46 extends through the lumen 42 of the extension sheath 38 and terminates at a location near the proximal tip 44 of the extension sheath 38. In other words, the guide wire 46 is contained within the lumen 42 of the extension sheath 38 and conforms to the shape of the extension sheath as the sheath is introduced and advanced though a patient's vasculature. The guide wire 46 and the extension sheath 38 are separate components, however, such that the extension sheath 38 may be removed from a patient's vasculature at some point during a procedure while the guide wire 46 remains in place within the vasculature.

Figure 5:
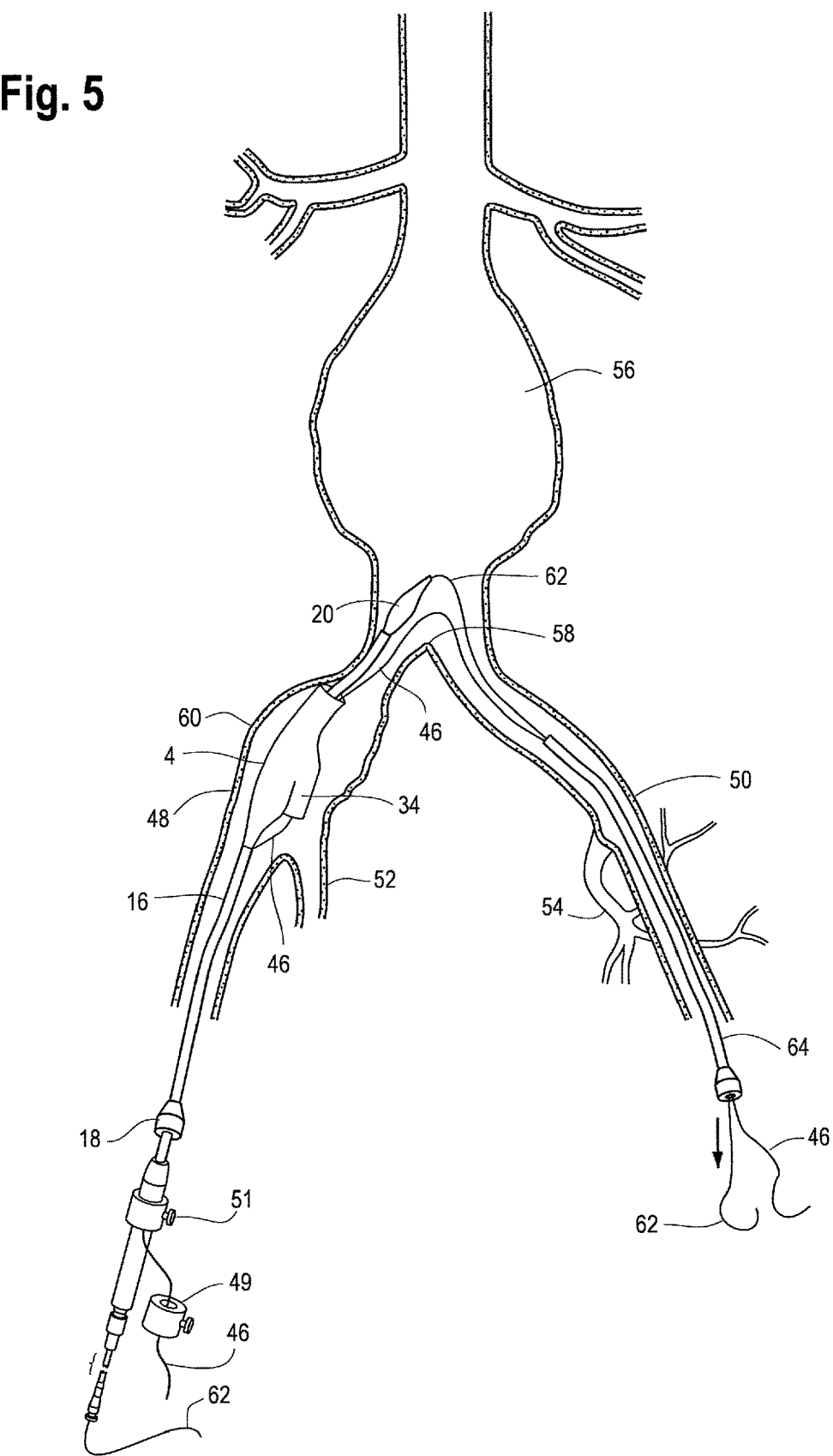
Figure 12:
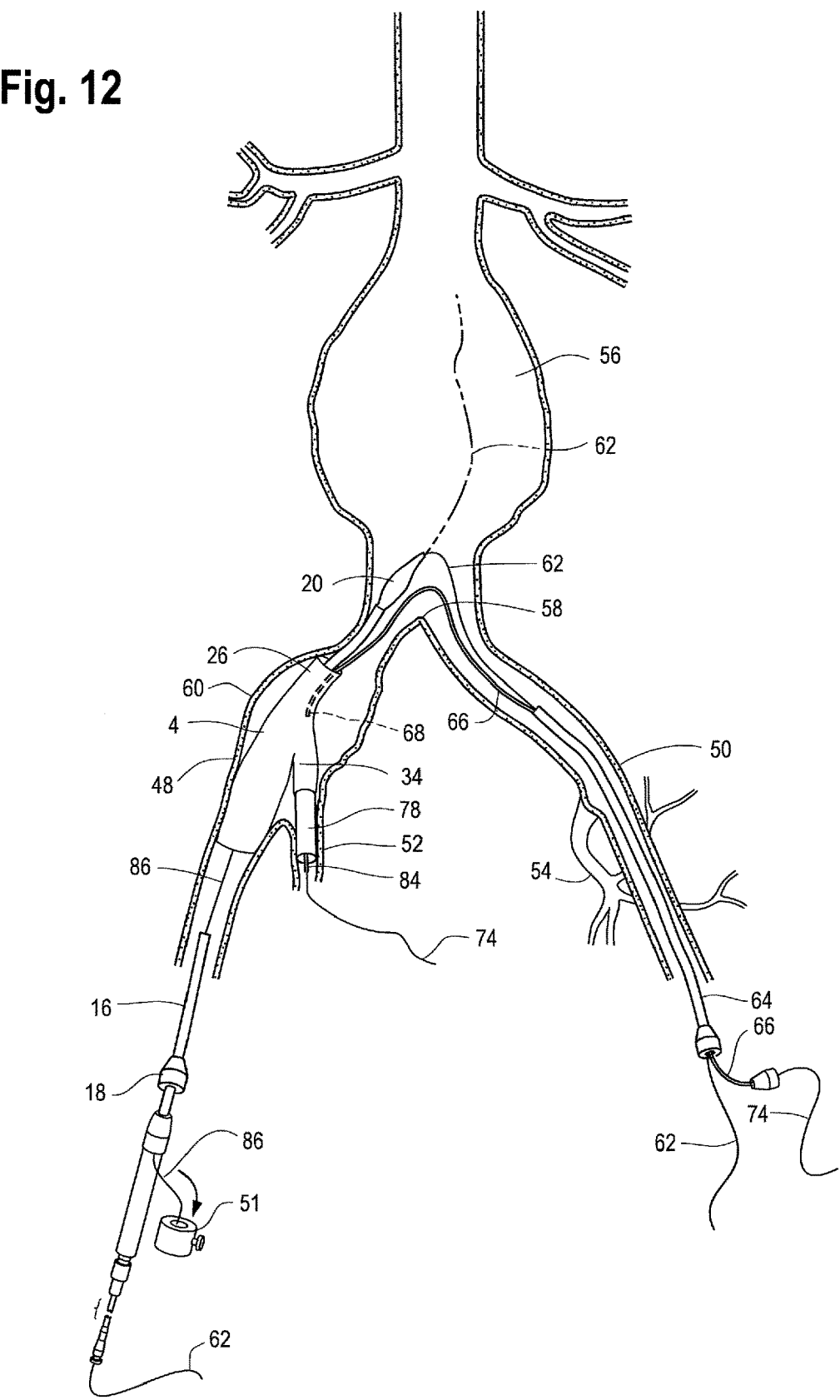

Looking to FIGS. 1 and 5, the device also preferably includes one or more control mechanisms 49 located outside of the patient's body at the distal end portion 8 of the delivery device 2 which allows the physician to manipulate the extension sheath 38 and, at the appropriate time during a particular procedure, release the extension sheath 38 from the delivery device 2 so that the extension sheath can be removed from the vasculature as described herein. One or more additional control mechanisms, such as mechanism 51 which is also preferably located outside of the patient's body as shown in FIGS. 1 and 12, can be acted upon by the physician to manipulate other components of the delivery device. In one non-limiting example, mechanism 51 may be connected to a distal end portion of one or more trigger wires or otherwise interface with the retention mechanism(s) that at least partially restrain and hold the stent graft 4 on the delivery device 2 prior to the final deployment of the graft 4 within the vessel lumen. Manipulation of control mechanism 51 preferably allows the removal of the trigger wire(s) and/or other retention mechanism(s) when it is appropriate or desirable to fully deploy the stent graft 4 in the vessel lumen during a particular procedure.

FIGS. 14-16 illustrate one example of a delivery device 102 comprising an extension sheath 138 and an extension cannula 148 which are configured to extend proximally from a nose cone 120. The nose cone 120 has a proximal end or tip 140 and a distal end 139 and a lumen 121 extending between the proximal and distal ends 140, 139. In one example, the proximal and/or distal ends 140, 139 of the nose cone 120 may have a constant outer diameter or in another example one or both of the proximal and/or distal ends 140, 139 of the nose cone 120 may taper radially inwardly. As shown in FIGS. 14 and 17, the distal end 139 of the nose cone 120 tapers radially inwardly in a distal direction while the proximal end 140 of the nose cone 120 has a substantially constant diameter (i.e., the proximal end 140 of the nose cone 120 does not taper in a proximal direction). Alternatively, the proximal end 140 may taper radially inwardly slightly in a proximal direction.

As shown in FIG. 14, the device 102 includes a pusher catheter 110 having a proximal end 112 and a distal end 114 with a lumen extending between the proximal and distal ends. A cannula 124 extends through the lumen of the pusher catheter 110, from the distal end 108 of the device to the nose cone dilator 120. The cannula 124 may extend substantially through the lumen 121 of the nose cone 120 and terminate just distal to the proximal end 140 of the nose cone dilator 120, or alternatively, the cannula 124 may terminate within the lumen 121 adjacent the distal end 139 of the nose cone dilator 120 as shown in FIG. 14. A stent graft 104 is releasably secured to the inner cannula 124. In one example illustrated in FIG. 14, the stent graft 104 is carried on the inner cannula 124 at a location proximal to the proximal end 112 of the pusher catheter 110 and distal to the distal end 139 of the nose cone.

An extension sheath 138 extends proximally from the proximal end 140 of the nose cone dilator 120. The extension sheath 138 has a proximal end 144, a distal end 143 and a body portion 141. The extension sheath 138 has an inner diameter of between about 8 French and about 12 French, thus defining a lumen 142 extending between the proximal and distal ends 144, 143 of the extension sheath 138. The extension sheath 138 may be constructed of various biocompatible materials including vinyl or urethane and the like, for example, that allows the extension sheath 138 to be flexible yet rigid enough to navigate through a patient's tortious vasculature.

An extension cannula 148 extends through the lumen of the extension sheath 138. The extension cannula 148 comprises a proximal end 150 and a distal end 152 and a lumen 154 extending therebetween. The extension cannula 148 may be constructed of various biocompatible materials including Nitinol, stainless steel (possibly with laser cuts to increase flexibility), PEEK, and the like. The extension cannula 148 may have an outer diameter that is less than the inner diameter of the extension sheath lumen 142, such that the extension sheath 138 encompasses and/or is coaxial with the extension cannula 148. As illustrated in FIGS. 14 and 15, the proximal end 150 of the extension cannula 148 may attach to an extension nose cone 156 and the extension cannula 148 extends longitudinally within the lumen towards the proximal end of the extension sheath 138. The extension nose cone 156 has a proximal end 162, a distal end 160 and a lumen 164 extending there between. For example, the extension cannula 148 may be secured to the extension nose cone 156 by one or more appropriate attachment mechanisms, including friction fit, adhesive connection or a screw/thread connection. If the screw/thread attachment method is used, the proximal end 150 of the extension cannula 148 may have threads (not shown) which correspond to and engage with threads (not shown) located within at least a portion of the lumen 164 of the extension nose cone 156. The extension cannula 148 may not necessarily extend all the way through the lumen 142 of the extension sheath 130 to the proximal end of the extension sheath 138, but may terminate anywhere along the length and/or within lumen 142 between the proximal and distal ends 144, 143 of the extension sheath 138.

The extension nose cone 156 may taper radially inwardly at its proximal end 162. The extension nose cone 156 may have a narrowed diameter portion 147 extending distally from the distal end 160 which has an outer diameter that is less than the outer diameter of the distal end 160 of the extension nose cone 156. This difference in outer diameters may be substantially equivalent to the wall thickness of extension sheath 138, such that extension sheath 138 may circumferentially surround the narrowed-diameter portion 147 of the extension nose cone 156, allowing the proximal end 144 of the extension sheath 138 to abut and lay flush against the distal end 160 of the extension nose cone 156 as shown in FIG. 14 to provide a smooth transition between the outer surface of the proximal end 144 of the extension sheath 138 and the outer surface of the extension nose cone 156. The extension sheath 138 may be releasably secured to the narrowed diameter portion 147 at the distal end 160 of the extension nose cone 156 by one or more appropriate attachment mechanisms including, for example, friction fit, snap fit, adhesives, threads and the like.

The outer diameter of the main body portion 141 of the extension sheath 138 may be relatively uniform along the length of the extension sheath 138. The distal end 143 of the extension sheath 138 may have an outer diameter greater than the outer diameter of body portion 141. More specifically, as shown in FIGS. 14 and 15, the extension sheath 138 may have a generally uniform outer diameter along the body portion 141, and have a radially outwardly flared distal end 143. For example the outer diameter of the body portion 141 of the extension sheath may be in the range of about 6 French to about 12 French and the outer diameter of the flared distal end 143 of the extension sheath 138 may increase one or more French sizes.

The outer diameter of the flared distal end 143 of the extension sheath 138 may be approximately equivalent to the outer diameter of the proximal end 140 of the nose cone 120. As shown in FIG. 14, the distal end 152 of the extension cannula 148 extends distally beyond the distal end 143 of the extension sheath 138. The lumen 121 of the nose cone dilator 120 is preferably sized and configured to receive at least a portion of the distal end 152 of the extension cannula 148 therein. Thus, as shown in FIG. 15, the extension cannula 148 can be releasably secured to the nose cone 120 when the distal end 152 of the extension cannula 148 is inserted into the lumen 121 at the proximal end 140 of the nose cone dilator 120. In one example, the distal end 152 of the extension cannula 148 may be inserted into the lumen 121 and mated with the proximal end 140 of the nose cone by friction fit, or alternatively or in combination, adhesives, threads or other mechanisms that allow the respective components to be removably secured to each other.

When the extension cannula 148 and nose cone 120 are mated, the proximal end 140 of the nose cone 120 is adjacent to and abuts the distal end 143 of the extension sheath 138 as shown in FIG. 15. In another example, the flared distal end 143 of the extension sheath 138 may extend further distally so that the distal end 143 of the extension sheath 138 does not just abut the proximal end 140 of the nose cone 120, but rather, the distal end 143 is coaxial with and covers at least a portion of the proximal end 140 of the nose cone 120. In other words, the distal end 143 of the extension sheath 138 may have an inner diameter of between about 8 Fr and about 12 Fr and may be configured to receive a portion of the proximal tip 140 of the nose cone dilator 120 therein. As previously mentioned, the outer diameter of the proximal end 140 of the nose cone may be substantially equivalent to the outer diameter of the flared distal end 143 of the extension sheath 138, thus, when the nose cone 120 is mated with the distal end 152 of the extension cannula 148, there a smooth transition between the outer surface of the nose cone 120 and the outer surface of the extension sheath 138 as illustrated in FIG. 15.

A main sleeve or sheath 116 may be mounted co-axially over the pusher catheter 110. The sheath 116 may be constructed of various biocompatible materials including for example, Nylon, PTFE and/or Teflon®. In a pre-deployment configuration shown in FIG. 16, the sheath 116 extends proximally to the nose cone dilator 120 and covers the stent graft 104 that is releasably attached to the proximal end of the inner cannula 124. A handle 122 and a sheath manipulator 118 is preferably located at the distal end 108 of the pusher catheter as shown in FIG. 14, which enables manipulation of various components of the device 102 including sheath 116. It is noted that sheath 116 has been removed from FIG. 14 for the sake of clarity, so as to illustrate the various components of the delivery device 102, including the stent graft 104 and nose cone 120, that underlies the sheath 116 when in a pre-deployment condition.

In a pre-deployment configuration, the main sheath 116 extends proximally from the sheath manipulator 118 to the nose cone 120 and is coaxial with and covers at least the distal end 139 of the nose cone dilator 120. Alternatively, the sheath 116 may extend further proximally to cover substantially all of the nose cone 120 as FIG. 16 illustrates. The sheath 116 may have an inner diameter of about 13 Fr to about 17 Fr and may taper radially inwardly at the proximal end 117. The angle of the taper of the proximal end 117 of the sheath 116 may substantially correspond with the angle of the radially outwardly flared distal end 143 of the extension sheath 138. As shown in FIG. 16, the proximal end 117 of the main sheath 116 is coaxial with and covers at least a portion of the flared distal end 143 of the extension sheath 138 when the distal end 152 of the extension cannula is mated with the proximal end 140 of the nose cone and when the distal end 143 of the extension sheath 138 is adjacent to or otherwise secured to the proximal tip 140 of the nose cone dilator 120. The inward taper of the proximal tip 117 of main sheath 116 creates a smooth transition between the main sheath 116 and the extension sheath 138. This smooth transition between the main sheath 116 and the extension sheath 138 has several advantages, including but not limited to facilitating atraumatic navigation of the device 102 within the vasculature while minimizing and/or substantially eliminating damage to vessel walls during delivery and deployment.

This configuration may also effectively retain or pinch the distal end 143 of extension sheath 138 between the outer surface of the nose cone dilator 120 and the inner surface of the main sheath 116, thus preventing the extension sheath 138 from releasing prematurely from the proximal end 140 of the nose cone 120 during delivery and deployment. As shown in FIG. 17, the nose cone dilator 120 may include a groove 166 extending along at least a portion of the outer surface of the nose cone 120. The groove 166 is sized to accommodate and receive guide wire 146 therein. This allows the guide wire 146 to extend over and along the outer surface of the nose cone 120 and extend proximally into the extension sheath 138 while sliding freely within the groove 166 before the main sheath 116 has been retracted (i.e., wire 146 can move longitudinally within the groove 166 when sheath 116 is in a pre-deployment position and the extension sheath 138 still retained between the outer surface of the nose cone dilator 120 and the inner surface of the sheath 116 as shown in FIG. 16.

FIG. 16 illustrates one example of a delivery device 102 in a pre-deployment configuration with sheath 116 extending proximally to and coaxially over the nose cone 120. The inner cannula 124 may extend to and through at least a portion of the lumen 121 of the nose cone dilator 120 as best seen in FIG. 15. The inner cannula 124 may be substantially similar in diameter as extension cannula 148, such that the distal end 152 of the extension cannula 148 may terminate adjacent to and/or abut and/or otherwise align with the proximal end of inner cannula 124 within the lumen 121 of the nose cone 120.

In this pre-deployment configuration, the distal end 152 of the extension cannula 148 may extend into the lumen 121 at the proximal end 140 of the nose cone 120, thereby releasably securing the extension cannula 148 and extension sheath 138 to the nose cone 140. In this way, a continuous pathway or lumen is created which extends proximally through the inner cannula 124, through nose cone lumen 121, through extension cannula lumen 154 and through lumen 164 of the extension nose cone 156. This continuous lumen may be sized and configured to receive one or more wires, sheaths and/or cannulas there through, including, but not limited to guide wire 46/146, through wire 62, auxiliary wire 72, and auxiliary wire 74 during a delivery and deployment procedure.

Now looking at FIGS. 2 through 13, there is schematically illustrated a series of vessels within the human body, including the common iliac arteries 48 and 50 and the respective internal iliac arteries 52 and 54. The systems and methods described herein find particular application in the delivery, placement and deployment of one or more stent grafts therein, although as discussed earlier, the disclosed systems and methods are not restricted to this particular purpose and may be used in a variety of applications as will be appreciated by one of skill in the art.

Figure 2:
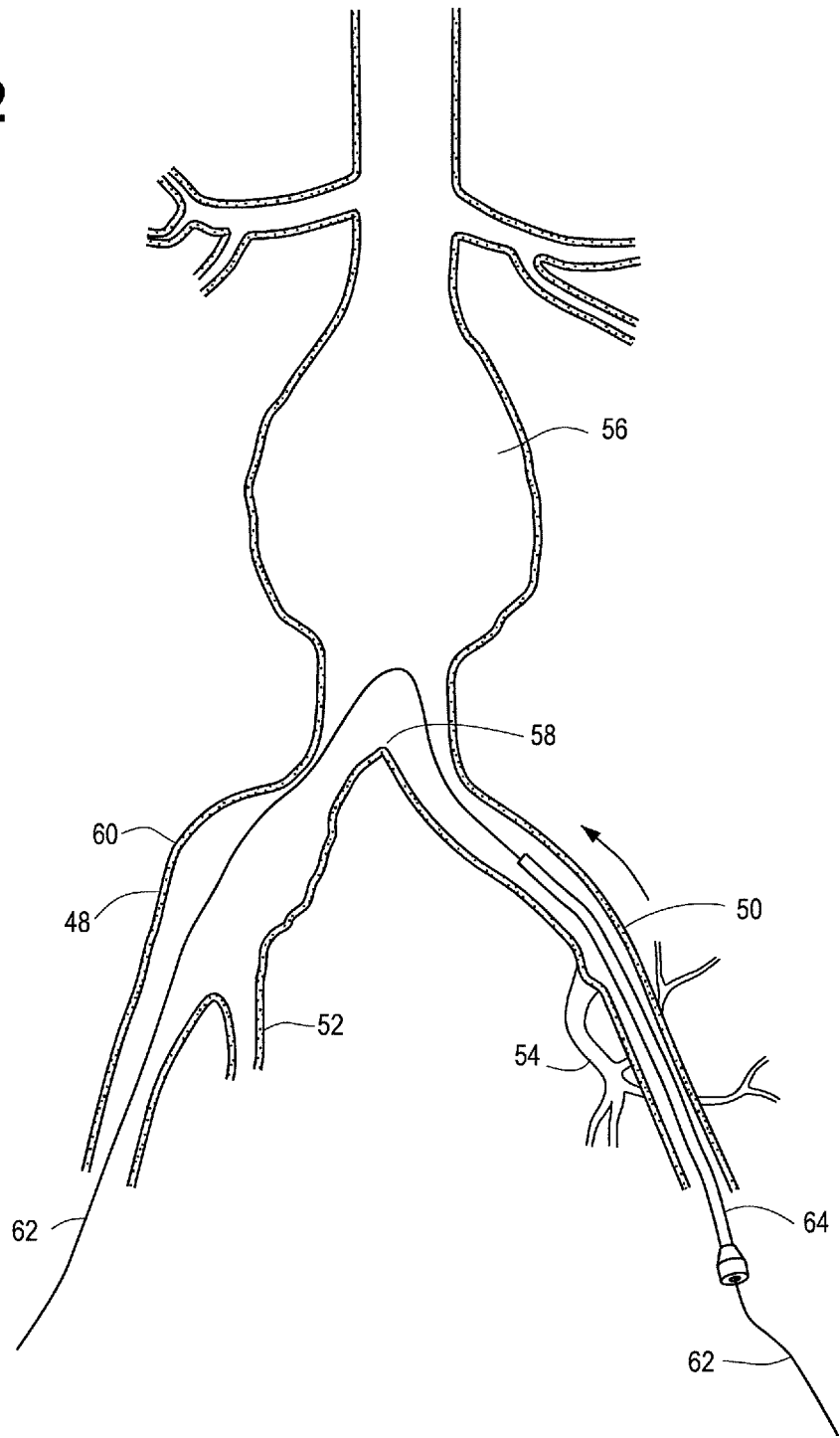
FIGS. 2-13 illustrate a portion of a patient's vasculature and an example of the various stages of the introduction, placement and deployment of a stent graft into a common iliac artery and an internal iliac artery.

Turning to FIG. 2, a descending aorta 56 extends down to an aortic bifurcation 58 from which extend common iliac arteries 48 and 50. From each of the common iliac arteries an internal iliac artery 52 and 54, respectively, extends. In most cases, the internal iliac arteries 52 and 54 cannot be practically accessed from their distal ends remote from the junction with the common iliac artery. For illustrative purposes, common iliac artery 48 is shown as having a diseased portion, including an aneurysm 60, although, it will be appreciated that one or both common iliac arteries 48, 50 and/or one or both internal iliac arteries 52, 54 may also include diseased portions that may be treated in accordance with the systems and methods described herein.

As shown in FIG. 2, the introduction of the delivery device 2 is preferably preceded by the placement of a "through wire" 62 within the vasculature of a patient, which provides an "up and over" pathway (i.e. a pathway extending proximally up through the contralateral iliac artery 50, over the aortic bifurcation 58 and distally down the ipsilateral common iliac artery 48). The pathway provided by the through wire 62 may be used to ultimately facilitate the introduction and placement of the delivery device 2 in a desired location with a vessel lumen, such as providing a pathway over which the delivery device 2 may be tracked or extended, for example. It is noted that the discussion herein in connection with the introduction and manipulation of delivery device 2 within the vasculature and methods of use thereof may also apply equally to the delivery device 102 as illustrated in FIGS. 14-17, thus, discussion of delivery device 2 and its various component parts may be interchangeable with the delivery device 102 and its equivalent components.

The through wire 62 may be placed in the vasculature by various acceptable methods and techniques, and introduced through various locations. In one non-limiting example, the through wire 62 may be introduced into a femoral artery via a femoral incision (not shown) and extended proximally beyond the aortic bifurcation 58 to the descending aorta 56. The wire may then be snared and pulled from the contralateral side to create the "up and over" pathway. Alternatively, the through wire 62 may be introduced into the vasculature through other locations, including, but not limited to through a brachial puncture (not shown) for placement in a desired location within the iliac arteries. As shown in FIG. 2, a portion of the through wire extends through the lumen of an auxiliary sheath 64 that is positioned in the contralateral iliac artery 50. Placement of the though wire 62 as shown in FIG. 2 by any number of acceptable techniques and methods aids in the introduction of the delivery device into the patient's vasculature as described in further detail below.

Figure 3:
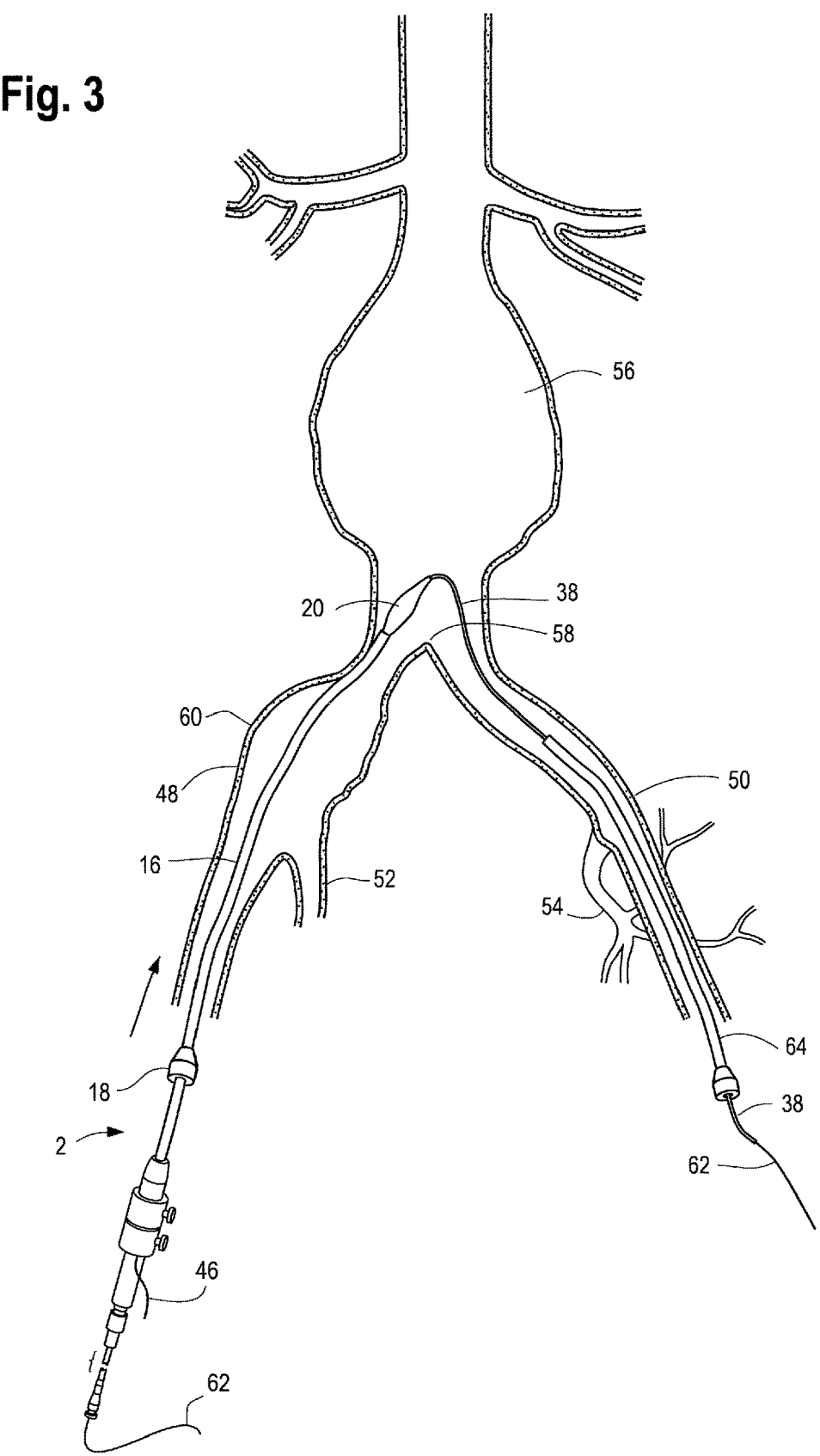

As shown in FIG. 3, the device 2 (and/or device 102 illustrated in FIGS. 14-17) may be introduced into the common iliac artery 48 and advanced over the through wire 62 with the nose cone dilator 20 (or 120) located near the aortic bifurcation 58. Preferably, the device is advanced so that the extension sheath 38 (or 138), with the preloaded guide wire 46 (or 146) enclosed within the lumen of the sheath 38, extends over the aortic bifurcation 58 and is tracked distally through the contralateral iliac artery 50 and through the auxiliary sheath 64 that remains in place in the contralateral iliac artery 50. At this stage, sheath 16 (or sheath 116), extending proximally up to the nose cone dilator 20, covers the branched stent graft 4 (104) that is carried on the device 2, so that the graft 4 is not visible in FIG. 3. With the device 2 in this position within the lumen of common iliac artery 48, the graft 4 (enclosed within the sheath 16) is preferably adjacent to the opening of the internal iliac artery 52.

Figure 4:
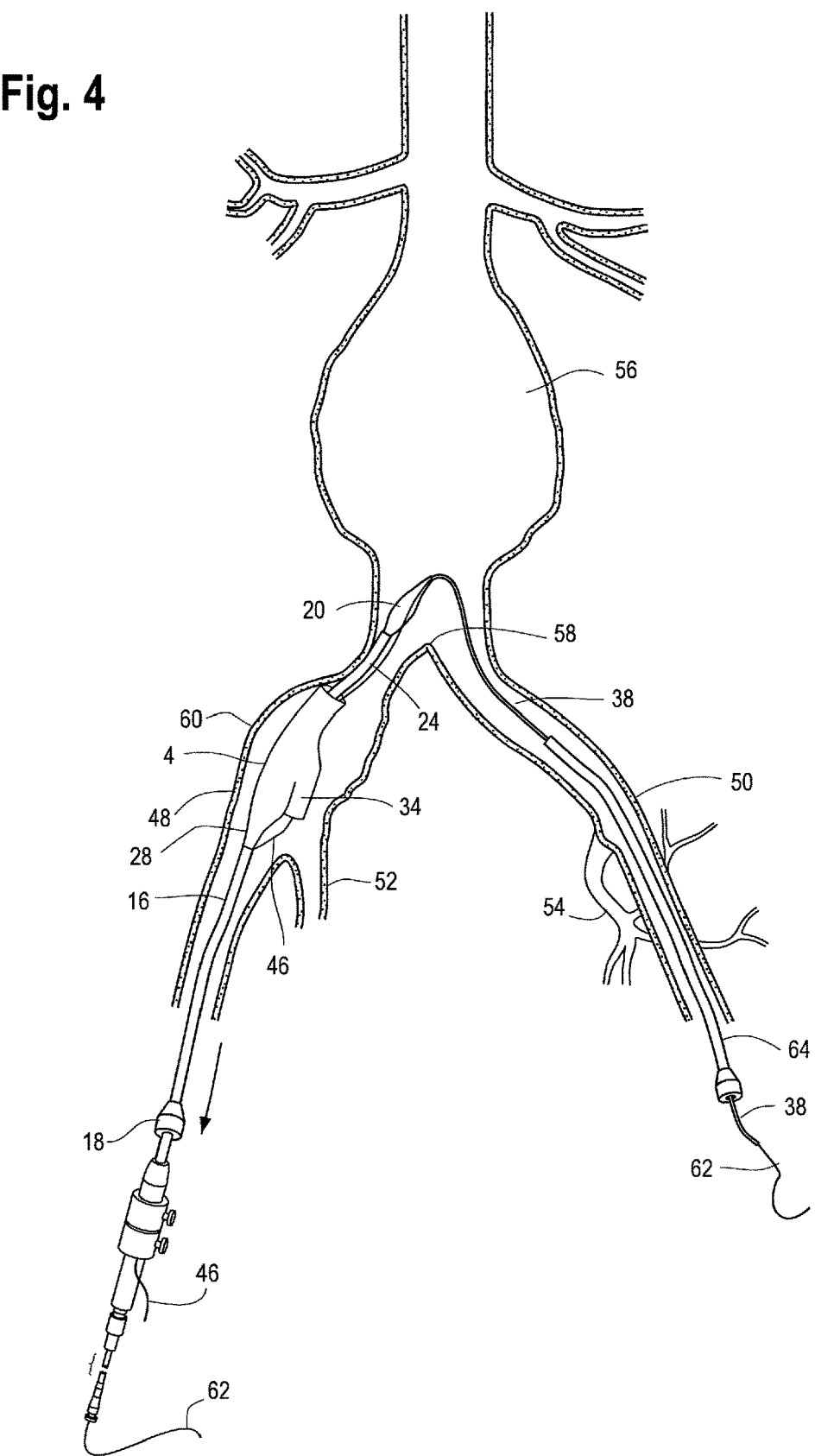

As shown in FIG. 4, the sheath 16 (116) has been partially withdrawn (in a distal direction) to expose the nose cone 20 (120) as well as the branched stent graft 4 (104) so that the sheath 16 is just distal of the distal end 28 of the graft 4. In the example shown in FIG. 16 where sheath 116 has a tapered proximal tip 117, this distal retraction of sheath 116 causing it to separate from the distal end 143 of the extension sheath 138 may require a force applied by the user's hand, such as in a range of about 20-80 Newtons. During separation of sheath 116 from the distal end 143 of the extension sheath 138, the flared proximal tip 117 of sheath 116 may deform radially outwardly and the distal end 143 of the extension sheath 138 may deform inwardly as the respective sheaths slide past one another.

The stent graft 4 is partially unconstrained in that it has been freed from the confines of the sheath 16, but it is still preferably retained by a retention mechanism at one or both of the proximal 26 and distal 28 ends of the stent graft. The graft may also include constraints or diameter reducing ties in the central portion, if desired. Accordingly, the stent graft 4 is not yet in a fully expanded condition within the lumen of the common iliac artery 48. It can be seen that the stent graft 4 carried on the device 2 is pre-loaded in one exemplary arrangement. More specifically, the device 2, with the stent graft 4 carried thereon, is pre-loaded as described above in connection with FIG. 1 (and/or in connection with device 102 illustrated in FIG. 14) such that the pre-loaded wire 46 extends proximally through the pusher catheter 10, through the lumen 36 of the side branch 34 of the stent graft, out of the proximal end 26 of the main graft body 4 and through the lumen 42 of the extension sheath 38. However, it is also contemplated that the device can be pre-loaded in a variety of acceptable ways that may not only aid in—the placement and deployment of the main stent graft 4 in the common iliac artery but which also ultimately facilitates the placement of one or more additional stent grafts into the branched vessels, including, but not limited to, the internal iliac artery.

FIG. 5 shows an example of the next stage a graft delivery and deployment sequence where the extension sheath 38 and extension cannula may be separated from the nose cone 20 (120) and removed from the patient's vasculature. (Although, it is also contemplated that the steps illustrated in FIGS. 4 and 5 could be reversed, such that the extension sheath 38 may be removed when sheath 16 has been distally retracted to expose at least a proximal portion of the nose cone 20 (120) but before graft 4 (104) is unsheathed.) In one example, the control mechanism 49 located outside of the patient's body at the distal end portion 8 of the delivery device 2 can be manipulated by the physician, so as to release the extension cannula 148 and/or the extension sheath 38 (138) from the nose cone 20 (120), thus allowing the extension cannula and the extension sheath to be separated from the device and removed from the vasculature. In other words, upon retraction of the sheath 16 (116), the nose cone 20 (120) may dilate, thus allowing the extension sheath 138 to be separated and released therefrom.

In one example, the user may push the extension cannula 148 and/or the extension sheath 38 (138) forward or proximally to separate these respective components from the nose cone 20 (120). Alternatively, the user may hold the extension cannula 148 and/or the extension sheath 38 (138) steady and in a fixed position within the vessel while simultaneously retracting the inner cannula 24 (124) and nose cone 20 (120) in a distal direction to separate the nose cone from the distal end of the extension cannula 148 and/or the extension sheath 38 (138). The extension sheath 38 may be withdrawn distally through the auxiliary sheath 64 (as shown by the arrow in FIG. 5) from the contralateral iliac artery 50, although, if desired or necessary, the extension sheath 38 may be withdrawn by other acceptable techniques and methods, and/or withdrawn through other locations. With the extension sheath 38 removed, the pre-loaded wire 46 preferably remains in place as shown in FIG. 5 such that it extends through the delivery device 2 (in the ipsilateral iliac artery 48), out the proximal end 26 of the main graft body 4, over the aortic bifurcation 58 and distally through the auxiliary sheath 64 (in the contralateral iliac artery 50).

In the example described above, at this stage, the pathway provided by the pre-loaded guide wire 46 is essentially parallel to the "up and over" pathway provided by the through wire 62, and as shown in FIG. 5, both the pre-loaded wire 46 and the through wire 62 each have terminal ends that can preferably be accessed on the outside of a patient's body on one or both of the ipsilateral and/or contralateral sides 48, 50. Wire 46 may allow a physician to introduce, manipulate and place a stent graft at a desired location within the patient's vasculature, such as in a common iliac artery, while control of both wires 46, 62 may assist in the introduction of additional stent grafts in a branched and/or side vessel.

At this stage, an additional or "contralateral" sheath 66 is introduced into the patient's vasculature, which is preferably intended to facilitate the delivery and deployment of an extension graft into the ipsilateral internal iliac artery 52. Alternatively, sheath 64 may be used instead of using an additional sheath 66 if sheath 64 has the appropriate properties, including, but not limited to being larger than the extension sheath that is introduced therethrough (as described in detail below) and is long enough to reach the contralateral iliac artery 50.

Figure 6:
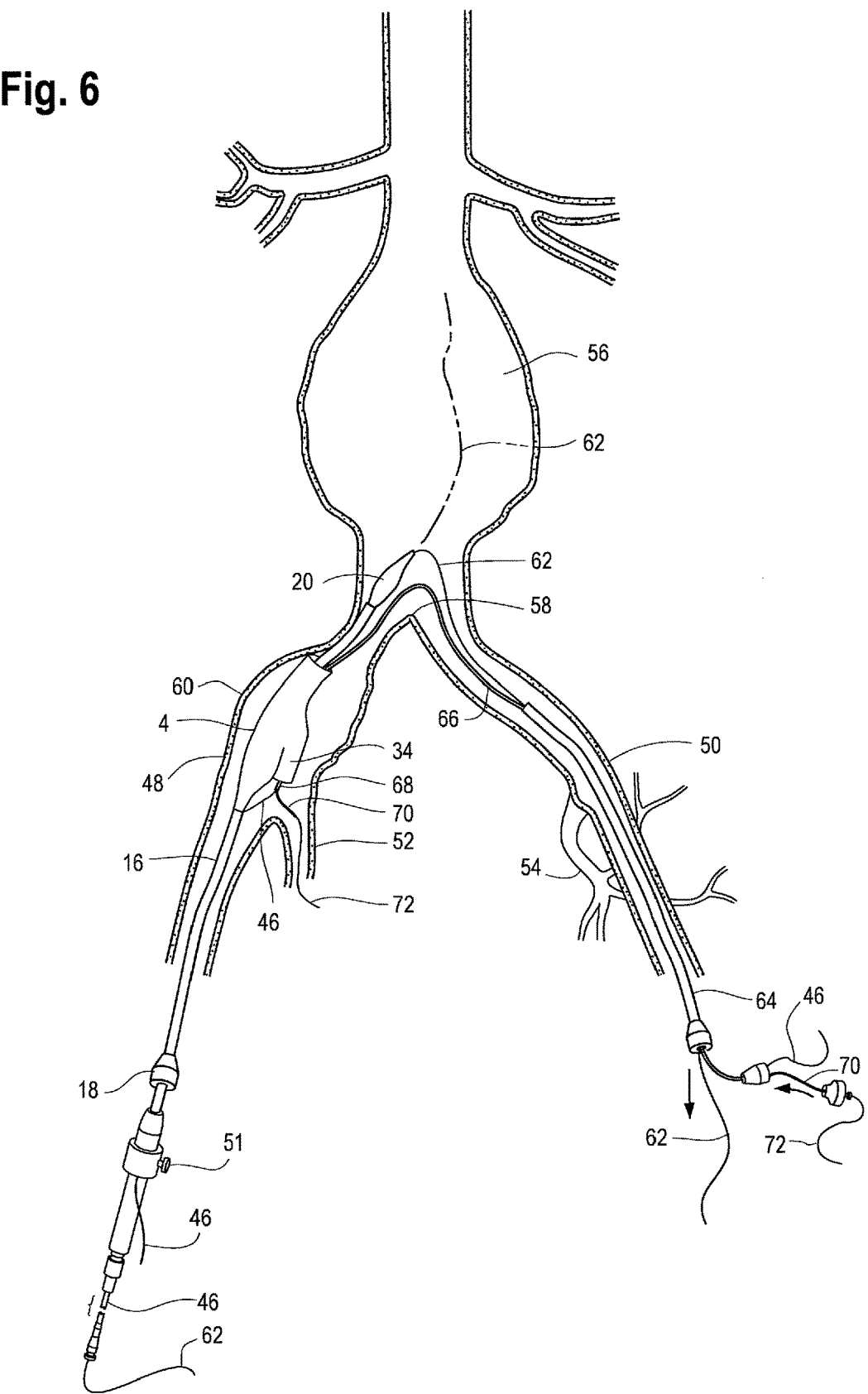

As illustrated in FIG. 6, a contralateral sheath 66 may be extended proximally through the contralateral iliac artery 50, over the aortic bifurcation 58, into the proximal end 26 of the main graft body 4 and through the lumen 36 of side branch 34. This may be accomplished by tracking the contralateral sheath 66 through the lumen of the auxiliary sheath 64 and over the pathway provided by the pre-loaded guide wire 46 (shown in FIG. 5) which is still in place in the iliac arteries 48, 50. As FIG. 6 best shows, the contralateral sheath 66 is extended until the tip 68 of the sheath 66 emerges from the distal end of the side branch 34 such that the tip 68 adjacent to the opening of the internal iliac artery 52. Alternatively, as FIG. 6 illustrates, the original throughwire 62 may be pulled in a proximal direction and advanced up into the infrarenal aorta 56, as shown by the dashed line in FIG. 6. With wire 62 extending proximally into the aorta 56 rather than distally through the contralateral sheath 66 (in contralateral iliac artery 50), space is freed up in the auxiliary sheath 64 (which would otherwise be taken up by the wire 62) to make room in the sheath 64 for the contralateral sheath 66 and auxiliary catheter 70 to be advanced therethrough.

Figure 7:
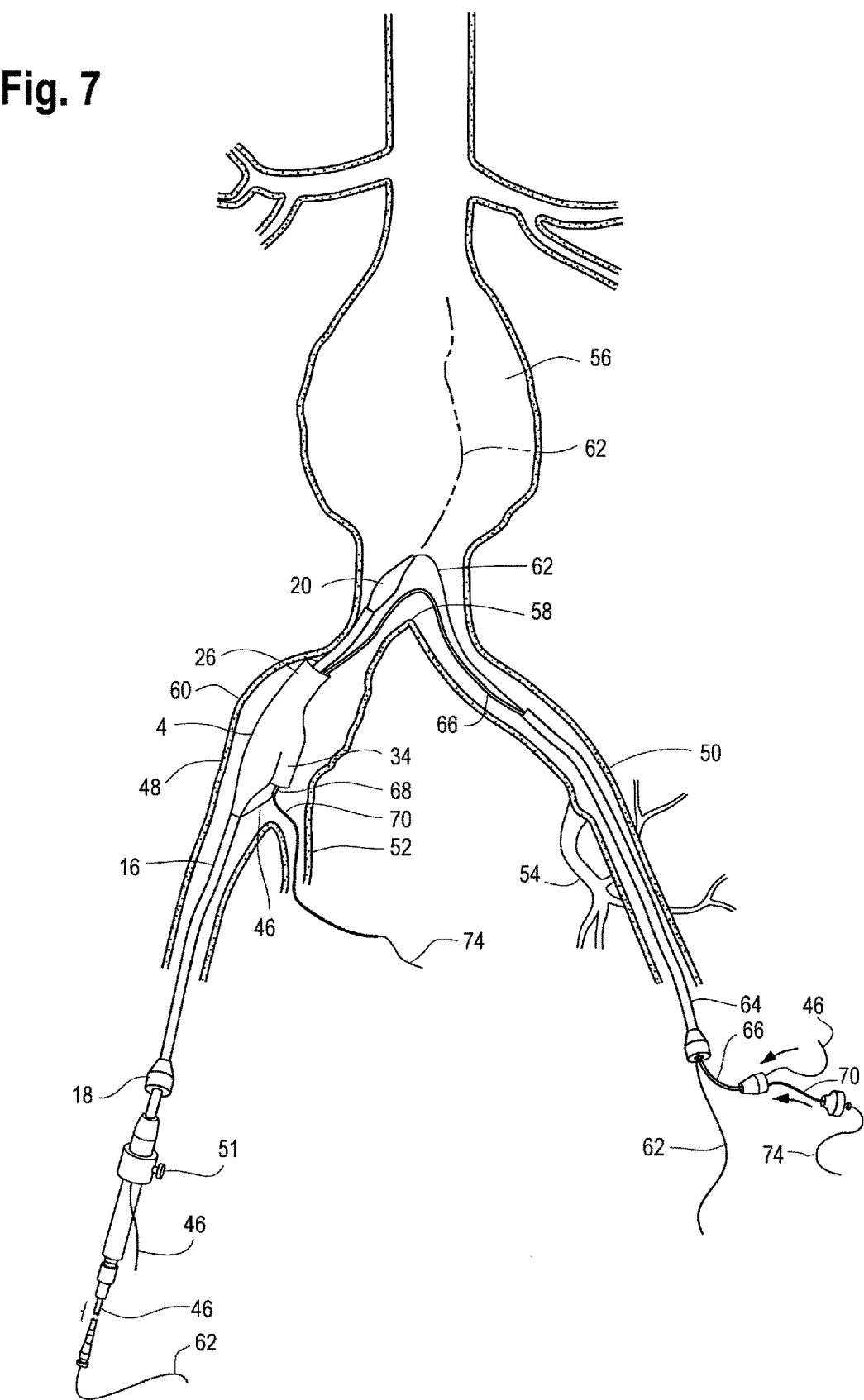

Auxiliary catheter 70, with an auxiliary wire 72 extending longitudinally through the lumen thereof, may be advanced all the way through the contralateral sheath 66 for cannulation of the internal iliac artery 52, as shown in FIG. 6. The original auxiliary wire 72 that extends through auxiliary catheter 70 and that is initially introduced into the internal iliac artery 52 (as shown in FIG. 6) may be replaced with an alternative, stiffer auxiliary wire 74, if desired, which may be extended further, along with the auxiliary catheter 70, into the internal iliac artery 52, as illustrated in FIG. 7.

Figure 8:
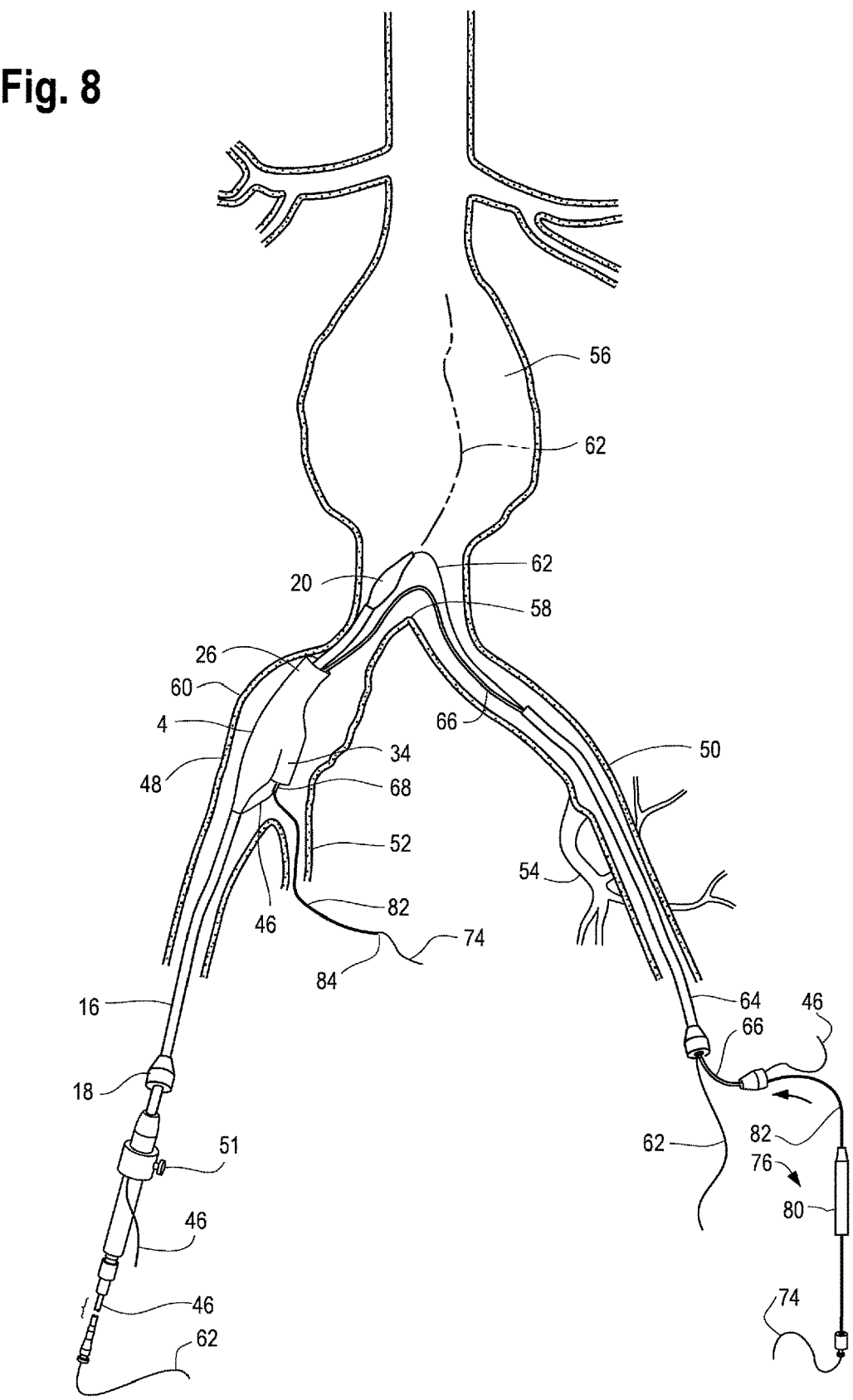

With the stiffer auxiliary wire 74 extended into and placed in a desired location in the internal iliac artery 52, the auxiliary catheter 70 can be withdrawn from the patient's vasculature as shown in FIG. 8. In one example, the auxiliary catheter 70 can be pulled distally through the contralateral sheath 66 (through the contralateral iliac artery 50) and removed from the vessel. The auxiliary wire 74 remains in place, however, after the auxiliary catheter 70 has been removed from the patient's body. At this stage, a second delivery device 76 can be tracked over the pathway provided by the auxiliary wire 74. The second delivery device 76 preferably carries an additional leg or "extension" stent graft 78 that is intended for delivery and deployment within the internal iliac artery 52, although extension graft 78 may be deployed within any portion of the patient's vasculature as necessary or desired. The extension graft 78 is preferably carried on a proximal end portion of the second delivery device 76, while a distal external manipulation portion 80 remains outside of the patient's body and allows a physician to manipulate the second delivery device 76 within the patient's vasculature. The extension graft 78 is preferably covered by an appropriately sized sheath 82 (so that the extension graft 78 is not visible in FIG. 8). The second delivery device 76 is tracked over the auxiliary wire 74 until the proximal end portion or tip 84 of the device 76 is extended beyond tip 68 of the contralateral sheath 66, into the internal iliac artery 52, and the extension graft 78 positioned in a desired location therein. Preferably, the extension graft 78 is positioned in the internal iliac artery 52 so that it extends both proximally and distally away from the location of an aneurysm, therefore, spanning and bypassing the diseased portion of the vessel.

Figure 9:
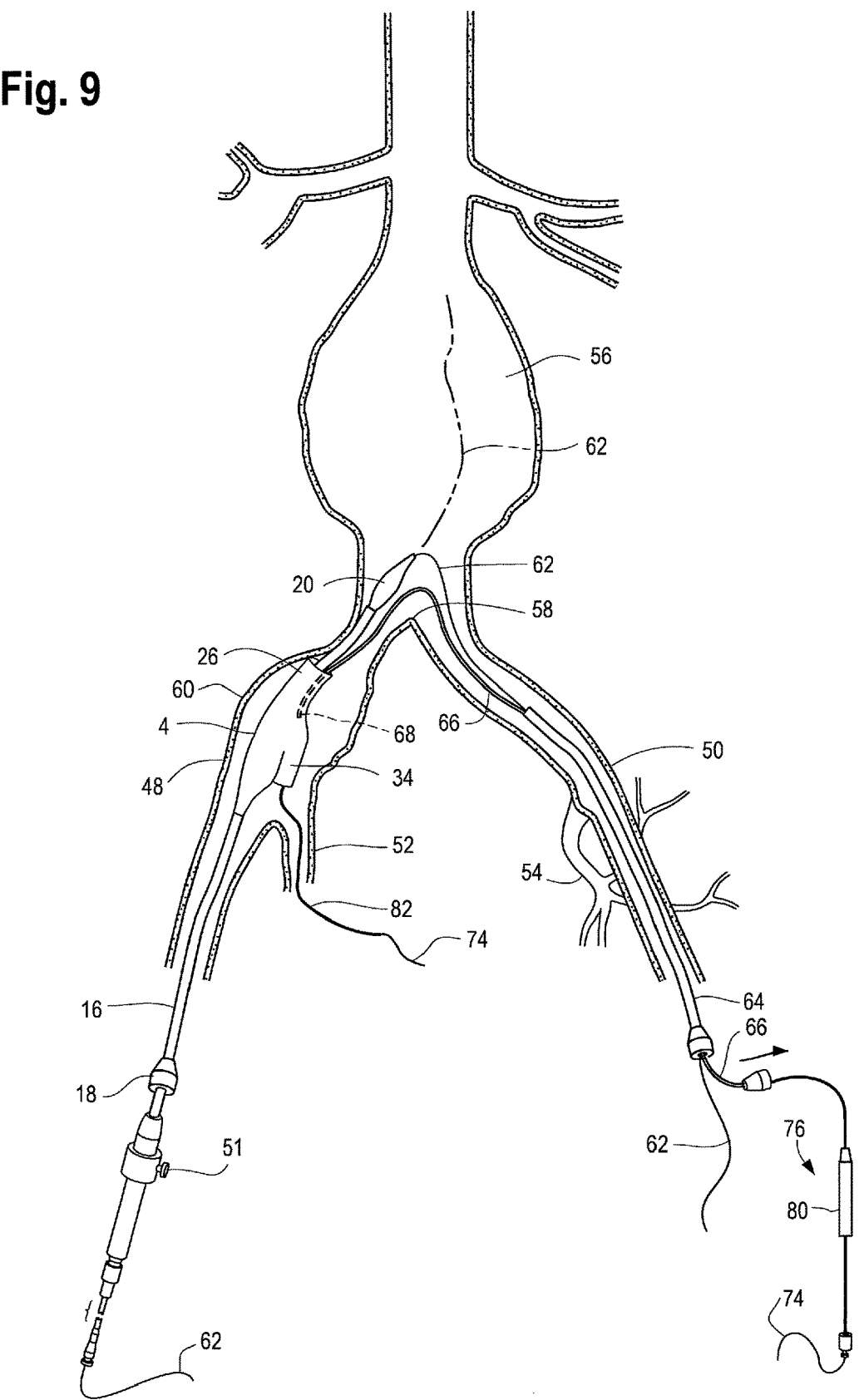

At this stage, the contralateral sheath 66 can be partially withdrawn, as shown in FIG. 9. In one example, the contralateral sheath 66 may be pulled distally from the contralateral side 50 until the tip 68 of the contralateral sheath 66 is located approximately adjacent to the proximal end portion of the side branch 34. At this time, the pre-loaded wire 46 may also be removed from the patient's vasculature. Preferably, this may be accomplished by pulling the pre-loaded wire 46 distally through the contralateral sheath 66 (within the lumen of the contralateral common iliac artery 50) and out of the patient's body. However, the pre-loaded wire 46 may also be removed in other suitable ways including through the delivery device 2 on the ipsilateral side 48.

Figure 10:
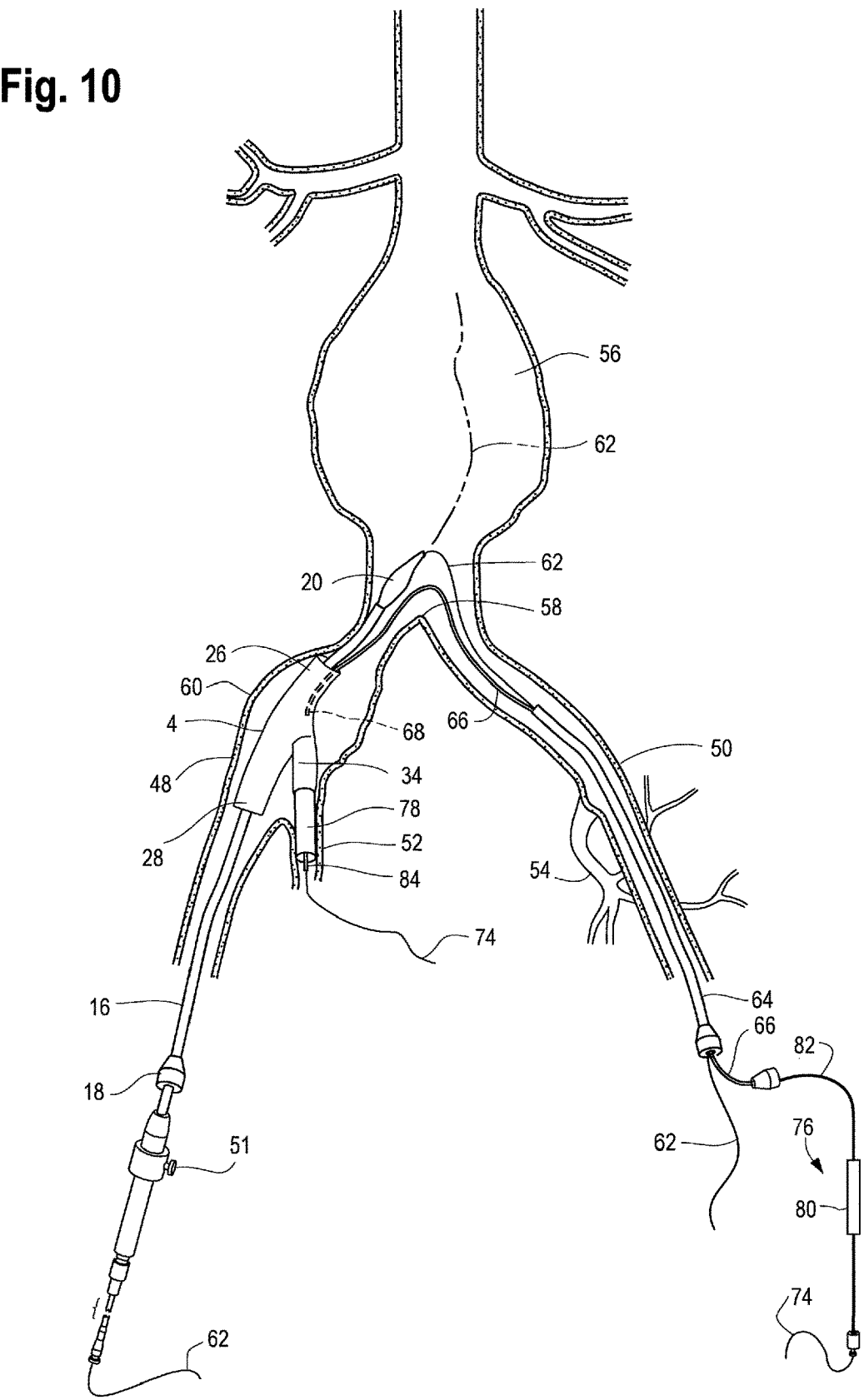
Figure 11:
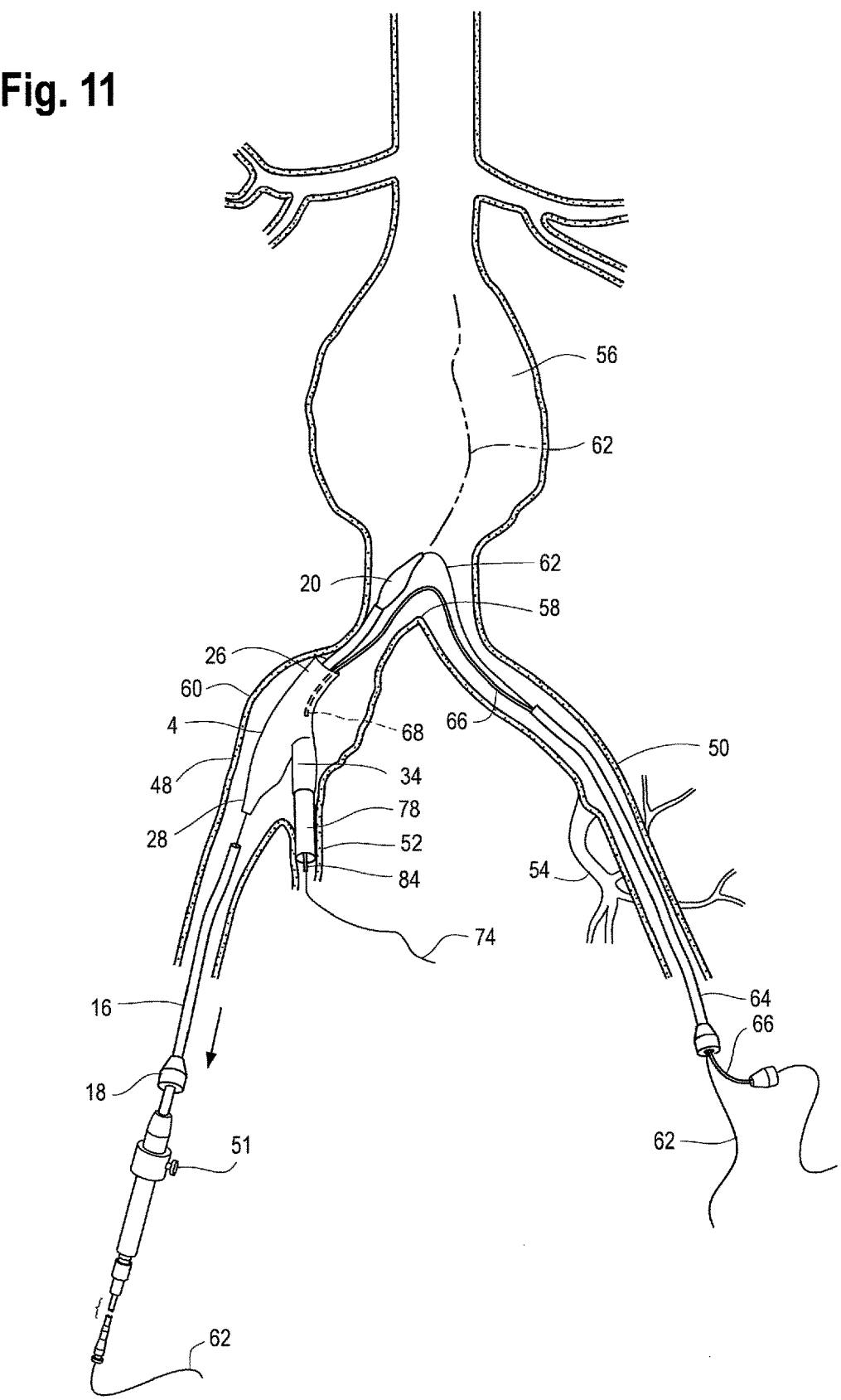

As shown in FIG. 10, the stent graft 4 and/or the extension graft 78 may be deployed within the lumen of the internal 52 and common iliac 48 arteries, respectively. For example, the sheath 82 covering the extension graft 78 on the second delivery device 76 may be withdrawn by pulling the sheath 82 distally through the contralateral sheath 66 for removal from the patient. At this time, the second delivery device 76 may also be removed from the patient's vasculature by pulling the second delivery device 76 distally through the contralateral sheath 66 (within the common iliac artery 50). In addition, the main sheath 16 (which covered the main stent graft 4 prior to delivery and deployment) may be withdrawn by pulling the sheath 16 distally from the ipsilateral common iliac artery 48 as shown in FIG. 11. After removal of the main sheath 16 from the main graft 4 and the extension sheath 82 from the extension graft 78, the grafts 4, 78 are at least partially deployed within the vessels 48, 52. To fully deploy the main 4 and extension grafts 78, the retention mechanism(s) that releasably retain the proximal end 26, the distal end 28 (or both ends) of the stent graft 4 on the delivery device 2, if present, are preferably removed.

To accomplish removal of the retention mechanism(s) when it is appropriate or desirable to fully deploy the stent graft 4 in the vessel lumen 48 during a particular procedure, the additional control mechanism 51 as shown in FIG. 12 for example, can be acted upon by the physician to manipulate and remove one of the trigger wire(s) 86 and/or other retention mechanism(s). Once the retention mechanism(s) (not shown) have been removed from the proximal 26 and/or distal ends 28 of the stent graft 4 (and/or from extension graft 78 if such retention mechanisms are present in the second delivery device 76), the respective grafts 4, 78 may be radially expanded or deployed within the respective vessels 48, 52.

In one example, a "self-expanding" stent expands primarily based on its own expansive force without the need for further mechanical expansion. More particularly, a stent made of a shape-memory alloy such as Nitinol may allow the stent graft 4, 78, 104 to return to a predetermined expanded configuration upon removal of a sheath (e.g., sheath 16 or 82) or other mechanism that maintains the stent graft 4, 78, 104 in its compressed, pre-deployment configuration. In another example, stents made of materials such as stainless steel may expand on their own accord once released from constraints holding them in their compressed state. Alternatively, a stent graft 4, 78, 104 may require further manipulation, mechanical or manual expansion, such as by balloon expansion by the user. In either case, it is contemplated that the stent graft 4, 78, 104 may expand or deploy only partially within the vessel lumen after removal of any retention mechanisms, such that additional expansion of the stent graft 4, 78, 104 may be desired or required, at which time the user may implement various known and acceptable techniques to fully deploy the graft 4, 78, 104 in the common 48 and/or branched vessel 52. Such fully deployed stent grafts 4, 78 and/or 104 are illustrated in exemplary FIG. 13.

Figure 13:
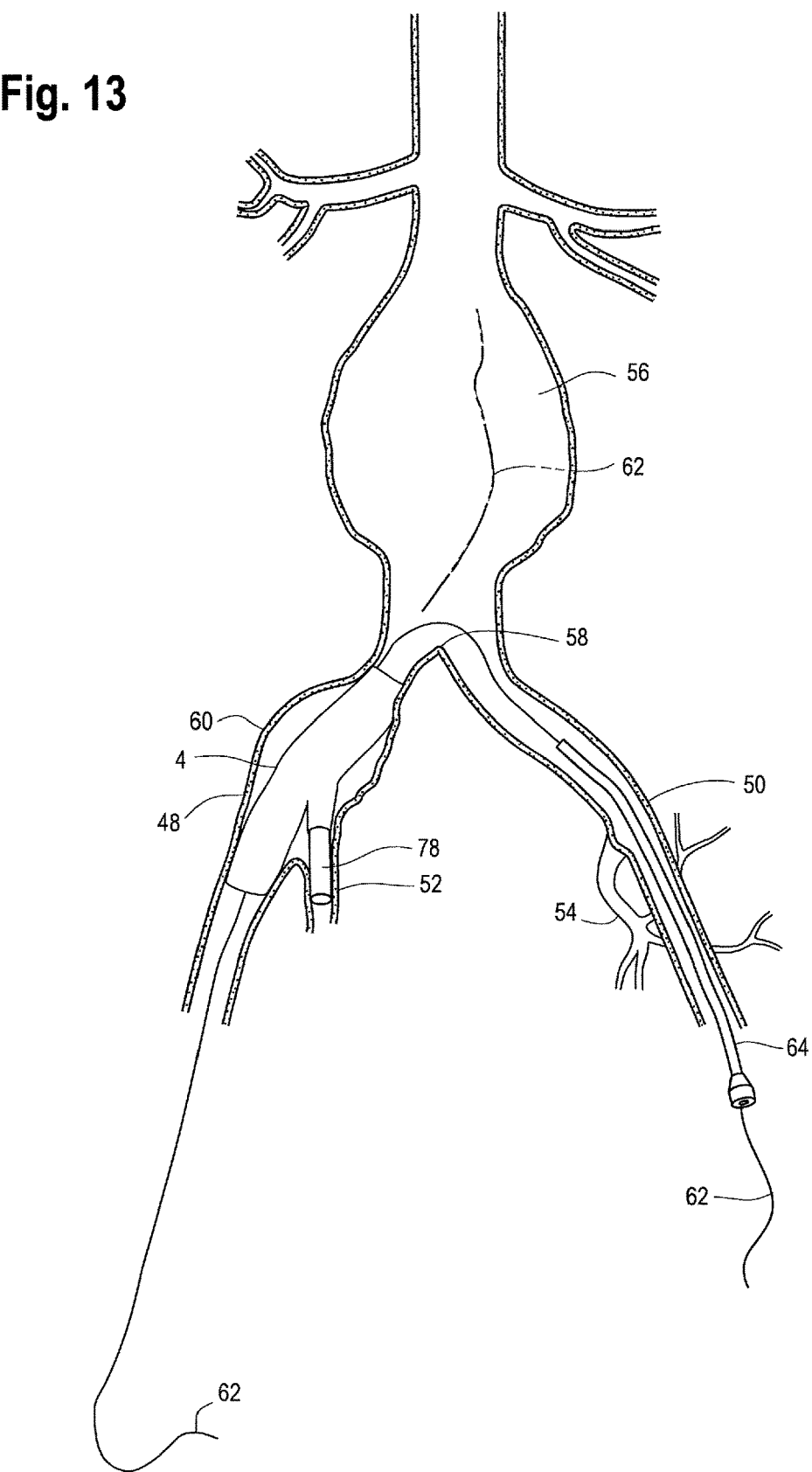

As shown in FIG. 13, the leg extension graft 78 preferably extends from the side branch 34 of the stent graft 4 into the internal iliac artery 52. Proximal and/or distal retention (not shown) of graft 78 may include the same or similar retention mechanisms as those described above in connection with the retention of stent graft 4 on delivery device 2, such that graft 78 may be retained on the second delivery device 76 in a manner similar to that of graft 4. Of course, other types and methods of proximal and/or distal restraint of extension graft 78 may be used including various diameter reducing ties, fasteners or the like that are suitable for removably securing the extension graft 78 on the further delivery device 76. Proximal and/or distal retention of extension graft 78 may be in addition to or in combination with sheath 82 which also secures the graft 78 to second delivery device 76 and holds it in a radially inwardly compressed "pre-deployment" condition.

Following graft deployment, the delivery device 2 can also be withdrawn from the patient's body, if desired, although in some situations, it may be desirable to leave one or more components, such as pusher catheter 10 and/or the sheath 16 in position within the common iliac artery 48 so that further introduction and deployment of another stent graft into the aorta 56, such as a bifurcated stent graft, can be facilitated through the pusher 10 and/or sheath 16.

Thus, the pre-loaded delivery device 2, 102 with an extension sheath 38, 138 as described herein effectively and efficiently facilitates the introduction, placement and deployment of a stent graft into one or more branched vessels, including, but not limited to a common iliac artery and an internal iliac artery extending therefrom, in order to treat and/or restore patency to one or both of such vessels.

While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together.

The invention claimed is:

1. A prosthesis delivery device comprising:
an inner cannula having a proximal end;
a nose cone dilator extending proximally from the proximal end of the inner cannula, the nose cone dilator having a proximal end and a distal end and a groove extending longitudinally along at least a portion of an outer surface of the nose cone dilator between the proximal and distal ends;
an extension cannula having a proximal end and a distal end releasably attached to the proximal end of the nose cone dilator;
an extension sheath coaxial with at least a portion of the extension cannula, wherein the extension sheath has a proximal end and a distal end and a lumen extending between the proximal and distal ends, and wherein the distal end of the extension sheath flares radially outwardly at an angle;
a main sheath having a proximal end, a distal end and a lumen extending therebetween, wherein the main sheath has a first position in which the proximal end of the main sheath is at least partially overlapping and coaxial with the distal end of the extension sheath and wherein the proximal end of the main sheath tapers radially inwardly at an angle and wherein the angle of the taper of the proximal end of the main sheath substantially corresponds with the angle of the radially outwardly flared distal end of the extension sheath, and a second position in which the proximal end of the main sheath is distal to the distal end of the extension sheath; and a pre-loaded guide wire extending proximally at least partially through the lumen of the main sheath, through the groove formed in the nose cone dilator and proximally at least partially through the lumen of the extension sheath.

2. The device of claim 1 wherein the proximal end of the nose cone dilator has an outer diameter and wherein the radially outwardly flared distal end of the extension sheath has an outer diameter that is substantially equal to the outer diameter of the proximal end of the nose cone dilator.

3. The device of claim 1 wherein the distal end of the extension cannula extends distally beyond the distal end of the extension sheath.

4. The device of claim 1 wherein the nose cone dilator further comprises a lumen extending between the proximal and distal ends of the nose cone dilator and wherein the distal end of the extension cannula extends at least partially into the lumen at the proximal end of the nose cone dilator when the extension cannula is releasably attached to the nose cone dilator.

5. The device of claim 1 wherein the proximal end of the main sheath deforms radially outwardly when the proximal end of the main sheath is coaxial with the distal end of the extension sheath.

6. The device of claim 1 wherein movement of the main sheath from the first position to the second position requires between about 20 Newtons to about 80 Newtons of force.

7. The device of claim 1 further comprising an extension nose cone dilator extending proximally from the proximal end of the extension sheath.

8. The device of claim 1 wherein the extension cannula is attached to the nose cone dilator when the main sheath is in the first position and wherein the extension cannula is separable from the nose cone dilator when the main sheath is in the second position.

9. The device of claim 1 wherein the distal end of the extension sheath abuts the proximal end of the nose cone dilator when the extension cannula is attached to the nose cone dilator.

10. The device of claim 1 wherein at least a portion of the proximal end of the nose cone dilator is received within the lumen of the distal end of the extension sheath when the extension cannula is attached to the nose cone dilator.

11. The device of claim 1 wherein the distal end of the extension sheath is retained between an inner surface of the main sheath and the outer surface of the nose cone dilator when the main sheath is in the first position.

12. The device of claim 1 further comprising a stent graft releasably coupled to the inner cannula at a location distal to the nose cone dilator and wherein the stent graft is held in a radially inwardly contracted condition by the main sheath when the main sheath is in the first position.

* * * * *